United States Patent [19]

Holmes

[11] Patent Number: 5,693,890
[45] Date of Patent: Dec. 2, 1997

[54] MODULAR ALIGNMENT DEVICE FOR TENSILE LOAD FRAME

[76] Inventor: John W. Holmes, 989 Forest Rd., Ann Arbor, Mich. 48105

[21] Appl. No.: 695,098

[22] Filed: Aug. 7, 1996

[51] Int. Cl.⁶ .................................................. G01N 3/20
[52] U.S. Cl. ................................... 73/856; 73/826
[58] Field of Search ........................... 73/856, 857, 858, 73/859, 860, 826

[56] References Cited

U.S. PATENT DOCUMENTS

| | | |
|---|---|---|
| 2,291,106 | 7/1942 | Ruch . |
| 3,204,451 | 9/1965 | Cavanaugh et al. ............... 73/859 |
| 3,593,573 | 7/1971 | Ely . |
| 3,724,266 | 4/1973 | Beckstrom . |
| 3,994,158 | 11/1976 | Weinhold . |
| 4,478,086 | 10/1984 | Gram . |
| 4,478,088 | 10/1984 | Loveland . |
| 4,535,636 | 8/1985 | Blackburn et al. . |
| 4,721,000 | 1/1988 | Scanlon . |
| 4,845,997 | 7/1989 | Radin et al. ...................... 73/856 |
| 4,869,112 | 9/1989 | Gram et al. . |
| 5,005,424 | 4/1991 | Markowski . |
| 5,054,324 | 10/1991 | Pohl .............................. 73/859 |
| 5,193,396 | 3/1993 | Gorski . |
| 5,279,166 | 1/1994 | Ward et al. ...................... 73/856 |
| 5,361,640 | 11/1994 | Carroll et al. . |

OTHER PUBLICATIONS

Engineering Fracture Mechanics, vol. 20. No. 1, pp. 159–167, 1984 Entitled "Drop in $K_1$ Due to Load Shift in Single–Edge–Notch Tests With Compliant Drawbars".

*Primary Examiner*—Richard Chilcot
*Assistant Examiner*—Max H. Noori
*Attorney, Agent, or Firm*—Dykema Gossett PLLC

[57] ABSTRACT

A load module for use with a uniaxial materials testing apparatus includes a module frame defining a rectangular opening therein defined by two opposed first sides and two opposed second sides, and a floating bracket disposed within the rectangular opening for movement between the first sides. A fixed grip for holding a first end of a test sample is rigidly attached to one of the first sides. A floating grip is rigidly fixed to the floating bracket on a side of the bracket facing the fixed grip. The floating grip for holding a second end of the test sample is axially aligned with the fixed grip. Linear bearings disposed between the second sides and the floating bracket are configured and located to constrain motion of the floating bracket to a single axis.

7 Claims, 2 Drawing Sheets

MODULAR ALIGNMENT DEVICE FOR TENSILE LOAD FRAME

FIELD OF THE INVENTION

This invention relates to the field of materials testing apparatuses, and more particularly to material testing apparatuses able to hold a test sample without bending the sample.

BACKGROUND OF THE INVENTION

Certain types of material tests, particularly uniaxial tensile creep test of material samples, require that the loading forces be maintained on a single axis, to prevent inducing even a small amount of bending load into the test sample. Even a small amount of bending load will cause the sample to fail at a different load and at a different rate than will pure axial loading. While known testing apparatuses have addressed bending, they do not eliminate all bending. If one end of the sample is rigidly fixed to a test apparatus frame, then a slight offset or angle of the direction of loading of the sample will produce a bending load in the sample. One attempt at eliminating bending introduced the use of a pivot at each end of the test sample. However, this eliminates all bending only if the sample deforms or fractures uniformly across a cross section transverse to the direction of tension. If it does not, then a bending load will be induced in the sample. For example, if a crack is initiated on one side of the sample, the centerline of loading of the double pivoted sample will change. This will alter the localized tensile stress at the root of the crack.

In addition to requirements for minimum bending, the tensile creep testing of brittle materials, such as ceramics and intermetallic materials, requires a loading system that is rigid in all directions perpendicular to the direction of loading. If compliance is present in directions transverse to the intended axial loading direction, the presence of cracks in a specimen that is under axial loading will cause a shift in the centerline of loading. The shift will change the driving force for crack extension, producing erroneous test results.

It is desired to provide a materials testing apparatus which substantially eliminates bending loads in test specimens during tensile loading to failure and which is rigid in all directions perpendicular to loading. It is further desired to provide a loading module which can be retrofitted into existing materials testing apparatuses and will substantially eliminate bending loads in test specimens during tensile loading.

SUMMARY OF THE INVENTION

A uniaxial materials testing apparatus includes a base, a crosshead, and at least two parallel laterally spaced side members connecting the base and the crosshead. A loading member extends past one of the base and the crosshead. A floating bracket is fixed to the loading member and is simultaneously disposed between the side members and between the base and the crosshead. A fixed grip for holding a first end of a test sample is rigidly attached to the other one of the base and the crosshead past which the loading member does not extend, and is disposed between the side members and facing the floating bracket. A floating grip for holding a second end of the test sample is rigidly fixed to the floating bracket on a side of the bracket which faces the fixed grip. The floating grip is axially aligned with the fixed grip. Linear bearings are disposed between the side members and the floating bracket, and are configured and located to constrain a motion of the floating bracket to a single axis.

A load module for use with a uniaxial materials testing apparatus includes a module frame defining a rectangular opening therein defined by two opposed first sides and two opposed second sides, and a floating bracket disposed within the rectangular opening for movement between the first sides. A fixed grip for holding a first end of a test sample is rigidly attached to one of the first sides. A floating grip is rigidly fixed to the floating bracket on a side of the bracket facing the fixed grip. The floating grip for holding a second end of the test sample is axially aligned with the fixed grip. Linear bearings disposed between the second sides and the floating bracket are configured and located to constrain motion of the floating bracket to a single axis.

The primary function of the disclosed device, when used with a creep frame, is to improve the degree of alignment that can be achieved when a rigid load-train is required for axial creep testing. Linear bearings are used to constrain motion in the axial loading direction of a test specimen. The device greatly increases the accuracy of the data when materials with a low failure strain such as ceramics are tested. These types of materials require very accurate alignment to minimize as much as possible any bending strains in the transverse direction. The device can also be used with loading frames used for tensile, compression and fatigue testing. An important feature of the loading/alignment device disclosed is that it is modular and can therefore be readily fit to existing creep frames and mechanical/servohydraulic load frames.

Accordingly, a materials testing apparatus is provided which substantially eliminates bending loads in test specimens during tensile loading. Also, a loading module is provided which can be retrofitted into existing materials testing apparatuses and which will substantially eliminate bending loads in test specimens during tensile loading.

DETAILED DESCRIPTION OF THE PREFERRED EMBODIMENTS

Figure 1:
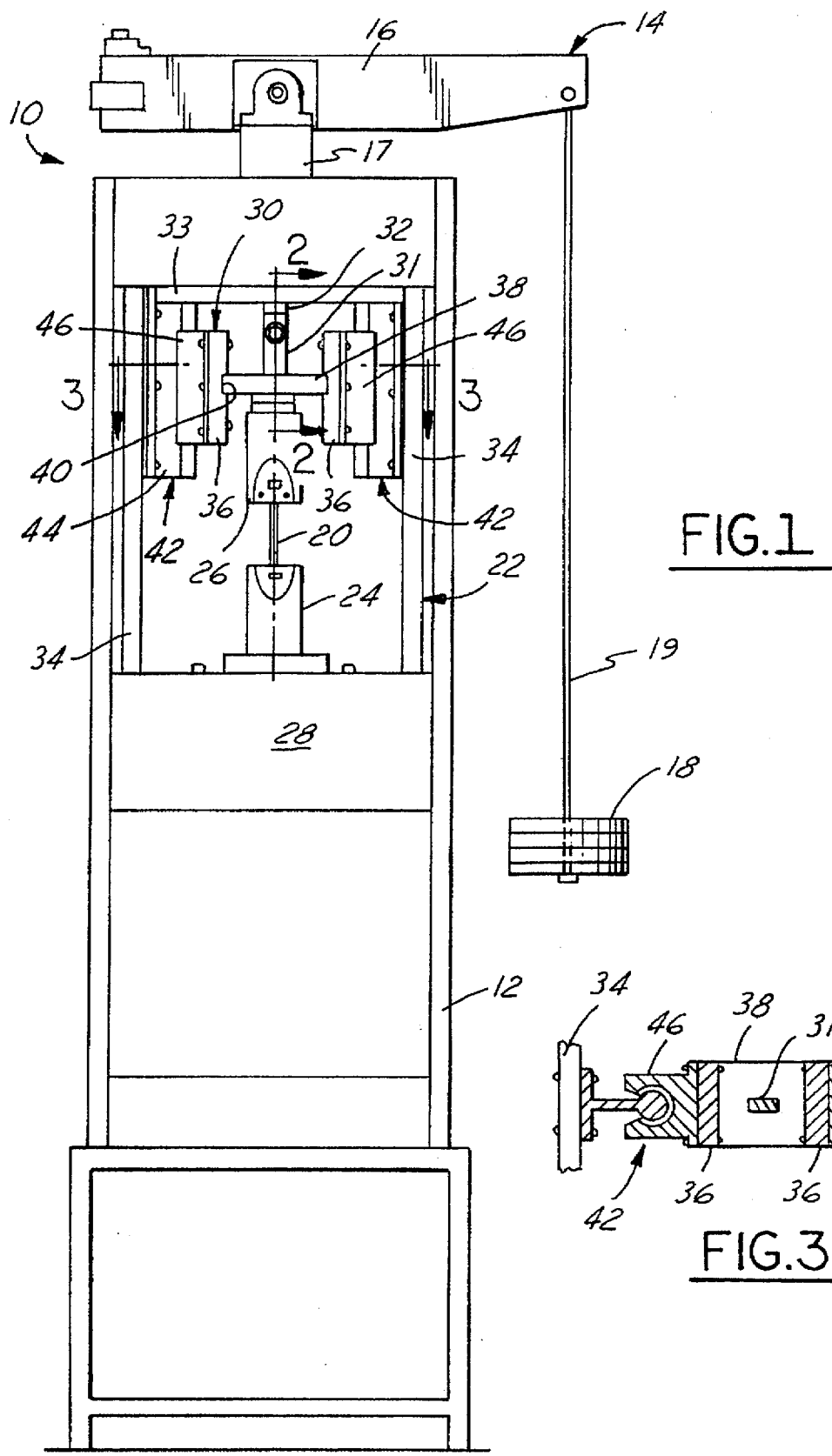
FIG. 1 is a frontal view of a creep test machine including a loading module.

A uniaxial materials testing apparatus 10 is shown in FIG. 1. The particular type of testing apparatus is a creep frame, or a creep test machine 10. Creep test machine 10 includes a supporting frame 12 and a loading mechanism 14. Loading mechanism 14 has a lever arm 16 supported on a top end of frame 12 by a pivot support 17. Weights 18 applied to a loading member 19 provide the force acting on a test specimen 20.

A loading module 22 is mounted within supporting frame 12. Specimen 20 is retained by a fixed grip 24 on a lower end and a floating grip 26 on an upper end. Fixed grip 24 is rigidly mounted to a base 28 fixed between side members of supporting frame 12. Floating grip 26 is mounted to an H-shaped floating bracket 30 which is in turn connected to lever arm 16 by a clevis 31 fixed to floating bracket 30. Clevis 31 is connected by a loading rod 32 to lever arm 16.

A crosshead 33 of loading module 22 is mounted to an upper portion of supporting frame 12. Loading rod 32 extends through an opening in crosshead 33. A pair of laterally spaced apart load module side members 34 are disposed inboard of the side members of supporting frame 12, and between base 28 and crosshead 33.

The floating bracket 30 has a pair of identical vertical members 36 and a connecting horizontal member 38. A channel 40 in each of vertical members 36 receives horizontal member 38. The relative position of the members 36 and 38 is maintained by welding them together. Floating bracket 30 is preferably made of aluminum, although other suitably rigid metals may be substituted therefor.

Figure 3:
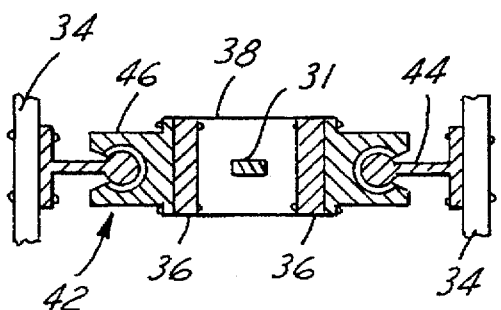
FIG. 3 is a sectional view of a portion of the loading module in the direction of arrows 3 of FIG. 1.

Identical linear bearings 42, as best seen in FIG. 3, are disposed between the load module side members 34 and vertical members 36. Each of linear bearings 42 includes a bearing shaft 44 fixed to its corresponding side member 34, and a bearing carriage 46 fixed to its corresponding vertical member 36.

Figure 2:
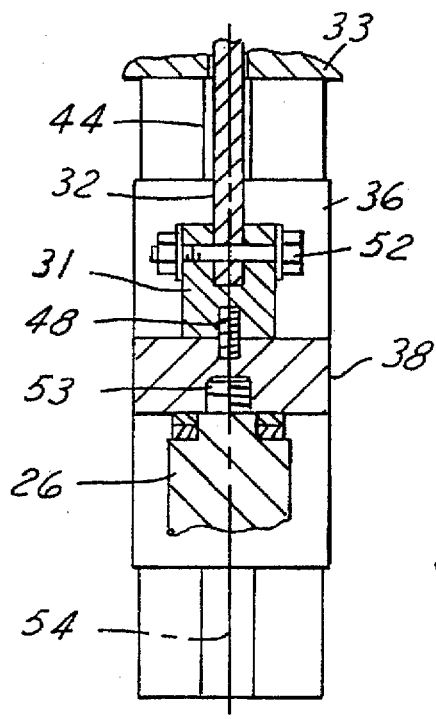
FIG. 2 is a sectional view of a portion of the loading module in the direction of arrows 2 of FIG. 1.

Clevis 31, as shown in FIG. 2, is fixed to horizontal member 38 by a threaded stud 48 threadably engaging both horizontal member 38 and clevis 31. Clevis 31 is pivotably attached to loading rod 32 by a bolt 52 passing through both parts 31 and 32. Floating grip 26 is also seen in FIG. 2 as being threadably fixed to horizontal member 38 by a stud 53 on the end thereof on a side opposite clevis 31. Loading rod 32, clevis 31, and floating grip 26 are all aligned on a common axis 54 with which fixed grip 24 is also in alignment. Axis 54 is located midway between load module side members 34.

Figure 4:
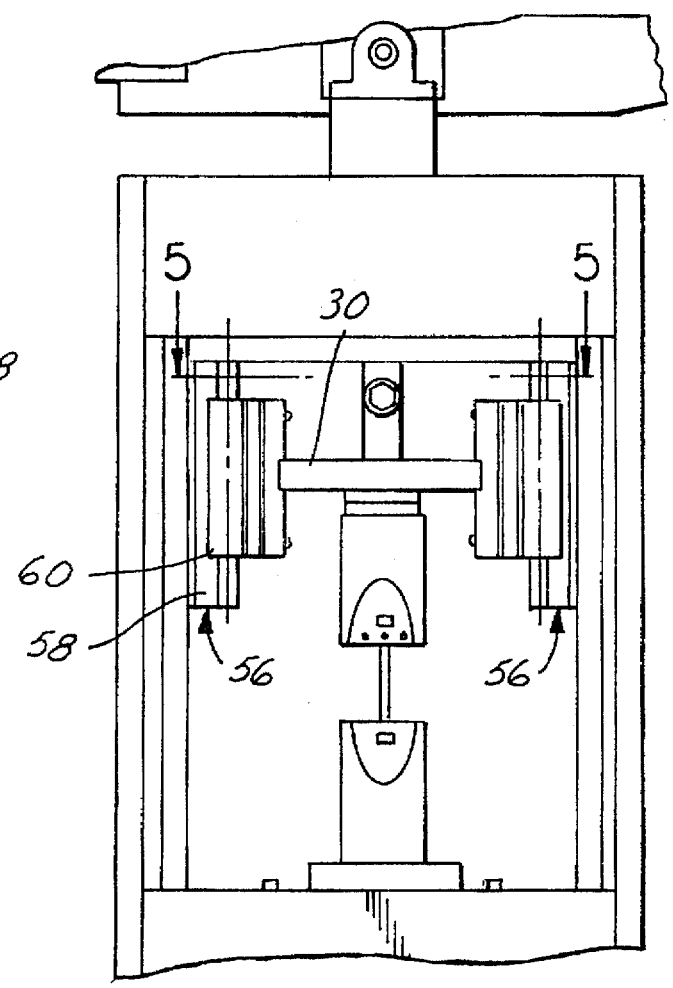
FIG. 4 is a broken out frontal view of a portion of a creep test machine including an alternative embodiment of the loading module.
Figure 5:
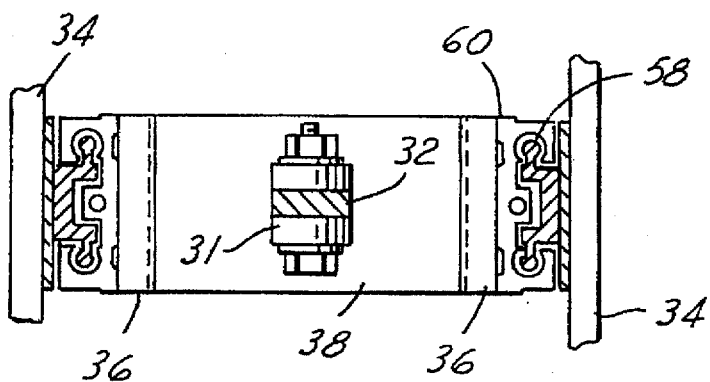
FIG. 5 is a sectional view of the loading module of FIG. 4 shown in the direction of arrows 5.

One alternative embodiment of the invention is illustrated in FIGS. 4 and 5. The embodiment of FIGS. 5 and 6 varies from that of FIGS. 1–3 only in the use of a different type of linear bearing 56.

This alternative linear bearing has a rail 58 and carriage 60 with a different cross-section as shown in FIG. 5. Linear bearings having cross-sections as shown in both FIGS. 3 and 5 are commercially available from bearing manufacturers.

The invention operates in the following manner. A test specimen is clamped on opposite ends by fixed grip 24 and floating grip 26 at a zero load condition. Load is increased to a testing level in a predetermined manner. As specimen 20 elongates, floating grip 26 consistently remains aligned with axis 54 as linear bearings 42 prevent any tipping or rotating of horizontal member 38. As specimen 20 begins to fracture, the applied load continues to substantially remain free of all bending with linear bearings 42 continuing to resist any tendency to tip or rotate horizontal member 38. With specimen 20 rigidly clamped by grips 24 and 26, and bracket 30 restrained by linear bearings 42, specimen 20 can be loaded to failure in pure tension.

Preferred embodiments have been disclosed. A worker of ordinary skill in the art would realize, however, that certain modifications would come within the teaching of this invention. For example, the loading module 22 could easily be integrated into a free standing tensile test machine or creep test machine. Specifically, side members 34 could be eliminated and the bearing shafts 44 mounted directly to the sides of supporting frame 12. With such a configuration, them would be no need for crosshead 33 of loading module 22, or a separate base 28. It should be appreciated that the type of grips shown is merely exemplary and other types may be employed. Further, the methods described for joining the parts together are exemplary only and may be substituted therefor. The following claims should be studied in order to determine the true scope and content of the invention.

I claim:
1. A uniaxial materials testing apparatus comprising:
a base;
a crosshead;
two parallel laterally spaced apart side members connecting the base and the crosshead;
a loading member extending past one of the base and the crosshead;
a laterally extending floating bracket fixed to the loading member and disposed between the side members and disposed between the base and the crosshead;
a fixed grip for holding a first end of a test sample being rigidly attached to the other one of the base and the crosshead and disposed between the side members and facing the floating bracket, the fixed grip being aligned with an axis;
a floating grip for holding a second end of the test sample being rigidly fixed to the floating bracket on a side of the bracket facing the fixed grip with the floating grip being aligned with the fixed grip along the axis; and
elongated linear bearings slidably connecting each side member with the floating bracket and the bearings configured and located to constraint a motion of the floating grip to movement along axis, a first of the bearings connecting the floating bracket with one of the side members and a second of the bearings connecting the floating bracket with an other of the side members wherein the elongated linear bearing prevent tipping and/or rotating the floating bracket with the floating grip resultantly remaining consistently aligned with the axis throughout travel of the floating bracket.

2. A testing apparatus as claimed in claim 1 with a clevis fixed to the floating bracket on a side of the bracket opposite the floating grip.

3. A testing apparatus as claimed in claim 1 wherein the floating bracket is H-shaped with the floating grip fixed to a horizontal portion of the bracket and with vertical portions of the bracket being connected to carriage portions of the linear bearings.

4. A load module for use with a uniaxial materials testing apparatus, the load module comprising:
a module frame defining a rectangular opening therein defined by two opposed first sides and two opposed second sides;
a floating bracket disposed within the rectangular opening for movement between the first sides, the floating bracket longitudinally extending between the second members;
a fixed grip for holding a first end of a test sample being rigidly attached to one of the first sides, the fixed grip being aligned with an axis;
a floating grip for holding a second end of the test sample, the floating grip being rigidly fixed to the floating bracket on a side facing the fixed grip and aligned with the axis; and
elongated linear bearings slidably connecting the second sides and the floating bracket, the linear bearing being configured and located to constrain motion of the floating grip to movement along the axis, a first of the bearings connecting the floating bracket with one of the side members and a second of the bearings connecting the floating bracket with an other of the side members wherein the elongated linear bearing prevent tipping and/or rotating of the floating bracket with the floating grip resultantly remaining consistently aligned with the axis throughout travel of the floating bracket.

5. A load module as claimed in claim 4 with a clevis fixed to the floating bracket on a side of the bracket opposite the floating grip.

6. A load module as claimed in claim 4 wherein the floating bracket is H-shaped with the floating grip fixed to a horizontal portion of the bracket and with vertical portions of the bracket being connected to carriage portions of the linear bearings.

7. A uniaxial materials testing apparatus comprising:

a supporting frame;

a loading mechanism disposed at one end of the supporting frame;

a load module disposed within the supporting frame including:
- a module frame defining a rectangular opening therein defined by two opposed first sides and two opposed second sides and with a portion of the loading mechanism passing through one of the first sides;
- a floating bracket disposed within the rectangular opening for movement between the first sides, the floating bracket longitudinally extending between the second members and connected to the portion of the loading mechanism passing through one of the first sides for displacement thereby;
- a fixed grip for holding a first end of a test sample, the fixed grip being rigidly attached to one of the first sides, the fixed grip being aligned with an axis;
- a floating grip for holding a second end of the test sample, the floating grip being rigidly fixed to the floating bracket on a side facing the fixed grip and aligned with the fixed grip along the axis; and
- elongated linear bearings slidably connecting the second sides and the floating bracket, the linear bearings being configured and located to constrain motion of the floating grip to a direction parallel to the axis, a first of the bearings connecting the floating bracket with one of the second sides and a second of the bearings connecting the floating brackets with an other of the second sides wherein the elongated linear bearings prevent tipping and/or rotating of the floating bracket with the floating grip resultantly remaining consistently aligned with the axis throughout travel of the floating bracket.

* * * * *

UNITED STATES PATENT AND TRADEMARK OFFICE
CERTIFICATE OF CORRECTION

PATENT NO.   : 5,693,890
DATED        : December 2, 1997
INVENTOR(S)  : Holmes

It is certified that error appears in the above-indentified patent and that said Letters Patent is hereby corrected as shown below:

Claim 1, column 4, line 28, delete "bearing" and insert --bearings--.

Claim 4, column 4, line 57, delete "bearing" and insert --bearings--.

Signed and Sealed this

Tenth Day of February, 1998

Attest:

BRUCE LEHMAN

Attesting Officer         Commissioner of Patents and Trademarks